United States Patent [19]

Richmond et al.

[11] Patent Number: 5,067,964
[45] Date of Patent: Nov. 26, 1991

[54] ARTICULAR SURFACE REPAIR

[75] Inventors: James W. Richmond, Kalamazoo, Mich.; John J. Block, Rumson, N.J.

[73] Assignee: Stryker Corporation, Kalamazoo, Mich.

[21] Appl. No.: 450,903

[22] Filed: Dec. 13, 1989

[51] Int. Cl.⁵ .............................................. A61F 2/30
[52] U.S. Cl. ..................................................... 623/18
[58] Field of Search ...................... 623/16, 18, 22, 23, 623/66, 11, 13

[56] References Cited

U.S. PATENT DOCUMENTS

| 4,502,161 | 3/1985 | Wall ........................ 623/18 |
| 4,642,120 | 2/1987 | Nevo et al. ............................. 623/16 |
| 4,674,488 | 6/1987 | Nashef et al. ...................... 623/16 X |

OTHER PUBLICATIONS

Medicarb (TM) Cartilage Repair System of Dunlop Medical Products (brochure copy).

Primary Examiner—David J. Isabella
Attorney, Agent, or Firm—Flynn, Thiel, Boutell & Tanis

[57] ABSTRACT

An articular cartilage repair piece and methods of forming and using same to substitute for a cut-out piece of damaged articular cartilage on a bone in an articulated joint in a mammal. The repair piece includes a backing layer of non-woven, felted fibrous material which is conformable to flat and curved surfaces. The front face of the backing layer is either uncoated or covered by a coating of tough pliable material having front surface which is tough, smooth and slippery in the presence of the natural synovial fluid of the joint and responds naturally as the repair site interfaces with underlying meniscus cartilage or articular cartilage of an opposing surface through articulating motion in the joint of a patient.

18 Claims, 2 Drawing Sheets

ARTICULAR SURFACE REPAIR

FIELD OF THE INVENTION

This invention relates to an articular surface repair and more particularly to an articular surface implant.

BACKGROUND OF THE INVENTION

The present invention was developed particularly in connection with repairing of injuries in the articular cartilage of a human knee joint. While the present invention is believed applicable to repair of similar injuries in the articular cartilage in other joints in humans and other mammals, for convenience same will be disclosed here in connection with repair of a defect in the articular cartilage covering a condyle of the femur in the knee joint of a human patient.

It has been known to employ a non-coated carbon fiber felt for articular surface repair. However, such is believed not to have proven entirely satisfactory.

Accordingly, the objects and purposes of this invention include provision of a method and apparatus for repair of a defect in the articular cartilage in a human or other mammal joint, for example on a condyle of the femur in a human knee joint, wherein usable materials include those used in other contexts in repairs in the human body and which have been approved by the FDA for other purposes within the human body, wherein such materials are commercially available, wherein such materials are of relatively low cost, wherein the completion of such a repair is within the skills of qualified orthopedic surgeons, and wherein alternative attachment techniques can be used in the repair.

Other objects and purposes of the invention will be apparent to persons knowledgeable in this art upon reading the following description and inspecting the accompanying drawings.

IN THE DRAWINGS

SUMMARY OF THE INVENTION

An articular cartilage repair piece and methods of forming and using same to substitute for a cut-out piece of damaged articular cartilage on a bone in an articulated joint in a mammal. The repair piece includes a backing layer of non-woven, felted fibrous material which is limp and readily conformable to flat and curved surfaces. The front face of the backing layer is covered by a coating of tough, pliable, elastomeric material having a front surface which is smooth and is slippery in the presence of the natural synovial fluid of the joint.

DETAILED DESCRIPTION

Figure 2:
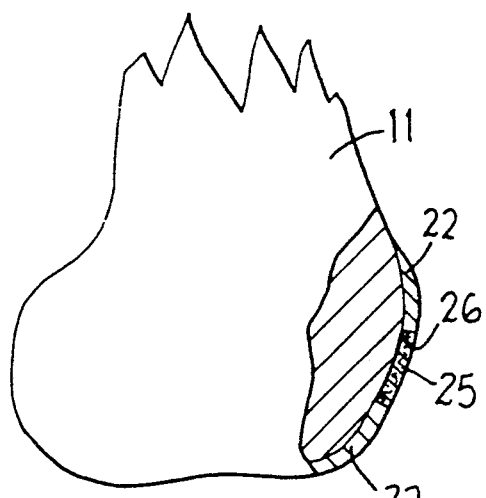
FIG. 2 is a side elevational view of the lower end of the femur of FIG. 1 and is partially broken away, in correspondence with the sectional line II—II of FIG. 1, to show in cross section a repair according to the present invention.

Although it is contemplated that the present invention is usable to repair defects in articular cartilage elsewhere in a human or other mammal body, for the sake of example, the invention is here illustrated in connection with repair of a defect in the articular cartilage on the femur in a human knee joint 10 illustrated in FIGS. 1 and 2.

Figure 1:
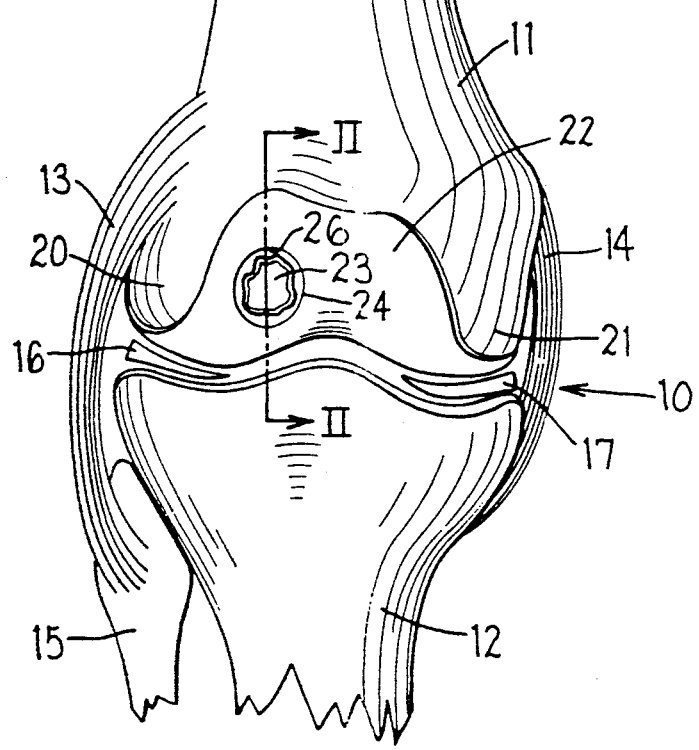
FIG. 1 is a fragmentary front elevational view of a human knee joint with sufficient tissue removed to show the articular cartilage on the condyles of the femur, and further showing a damaged area in such articular cartilage requiring repair.

Thus, FIG. 1 illustrates a knee joint 10 between the bottom of a femur 11 and the top of a tibia 12. For clarity of illustration, only portions 13 and 14 of the connective tissue which movably ties the femur 11 to the underlying tibia 12 and fibula 15, is shown in FIG. 1. Normally interposed between the opposing surfaces of the femur 11 and tibia 12 are lateral and medial meniscus cartilages 16 and 17. The convexly curved condyles 20 and 21 at the lower end of the femur 11 are normally supported by the meniscus cartilages 16 and 17, respectively, on the upper end of the tibia 12. Normally, the lower end of the femur 11, including the condyles 20 and 21, are covered by a layer 22 of cartilage material, referred to as the articular cartilage 22. The articular cartilage 22 forms a generally resilient padding which is fixed on the surface of the lower end of the femur 11 to protect the latter from wear and mechanical shock. Moreover, the articlar cartilage 22, when lubricated by the fluid in the knee joint 10, provides a surface which is readily slidable on the underlying surfaces of the meniscus cartilages 16 and 17 (or on the upper surface of the tibia 12 should one or both of the meniscus cartilage 16 and 17 be partly or totally absent) during articulation of the knee joint 10.

A portion of the articular cartilage may become damaged (for example, be torn or holed) or become excessively worn. FIG. 1 illustrates an example of a damaged area 23. Applicant has noted that it is desirable to repair such damage before it can spread or result in eventual injury or wear to the underlying condyle 20 or 21 or opposing tissues of the meniscus cartilage 16 or 17 or tissues associated with the facing portion of the tibia 12.

Generally, the present invention contemplates repairing the damaged area 23 by removing a conveniently shaped (here, for example, circular) portion 24 of the articular cartilage layer 22, including the damaged area 23. The size of the removed portion 24 is minimized, but it is large enough to include the entirety of the damaged area 23 therein. By making the removed portion 24 of regular shape (e.g., a circle, a square, etc.) it is easier to correctly shape and size a repair piece (implant) 25 hereafter described in more detail.

Following removal of the articular cartilage portion 24 including the damaged area 23, a correspondingly sized and shaped repair piece 25 (FIG. 2) is inserted into the opening 26 left in the articular cartilage layer 22 upon removal of the portion 24 therefrom. The repair piece 25 is temporarily held in place by means hereinafter described, until such time as tissue ingrowth, from the surface of the femur 11 and adjacent edges of the articular cartilage layer 22 surrounding the opening 26, more permanently fix the repair piece 25 in place.

The similar size and shape (in plan) of the removed cartilage portion 24 and repair piece 25 can be achieved in alternative ways. The surgeon may remove only the damaged cartilage area and cut the repair piece to the shape of the latter. Alternately, as above discussed, the surgeon may remove a regularly shaped piece of cartilage including the damaged area and cut a repair piece to that shape. Alternately, the surgeon may be provided in advance with several precut repair pieces of different sizes and/or shapes, and may then remove a piece of cartilage (including the damaged area) identical to one of the precut repair pieces. In the latter two alternatives the surgeon's shaping of the cartilage piece to be removed and/or repair piece may be "by eye" as in the first alternative. However, preshaped "cookie-cutter" type tools may instead be provided, the surgeon selecting the desired size and shape of "cookie-cutter" to remove the cartilage piece and cut the repair piece. Also, it may be possible to provide a variable size "cookie-cutter" tool, e.g. an expansible circle shaped one instead of plural different sized ones.

Figure 3:
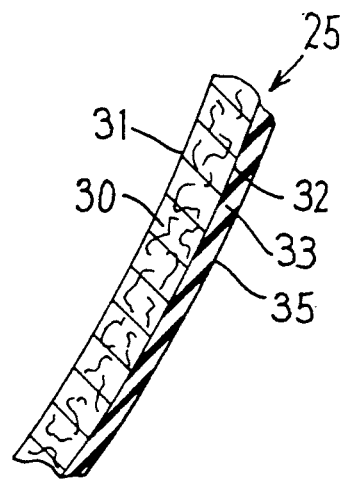
FIG. 3 is an enlarged fraction of FIG. 2 showing the repair piece (implant) in cross-section.

Turning now to the inventive repair piece 25 (FIG. 3) in more detail, same is cut to the desired shape and size from a previously prepared, wider panel (not shown). In the preferred embodiment shown, the repair piece (and the panel from which it is cut) is a substantially constant thickness laminate.

Such laminate comprises a non-woven, felted backing layer 30 (FIG. 3) having a back face 31 intended to engage the surface of the condyle 20 where the portion 24 of the articular cartilage 22 has been removed. A backing layer thickness in the range of 1 to 10 mm is contemplated. In the preferred embodiment shown, the felted backing layer is of felted polytetrafluoroethylene (e.g. Teflon TM ). The backing layer 30 has a front face 32. The laminate further comprises, in the preferred embodiment shown, a polyether urethane (hereinafter polyurethane or urethane) coating 33 covering and bonded to the front face 32 of the backing layer 30.

In one repair piece 25 constructed according to the invention, the felted Teflon TM backing 30 had a nominal thickness of about 1.2 mm and was obtained from Meadox Medicals, Inc. located at Oakland, N.J. Such felt has been used previously in ventricular aneurysmectomy, and tissue prosthesis, and suture buttressing, according to Meadox.

It is also contemplated that a polyester (e.g. Dacron TM ) felt material could be used for the backing 30. However, the Teflon TM felt material is preferred because it is a much more flexible material and results in a finished repair piece 25 that is more flexible and more conformable to curved or other irregular surfaces.

In the same unit according to the invention, the polyurethane coating 35 was obtained from Cardiac Control Systems, Inc. of Palm Coast, Fla., as a 20% solution of polyetherurethane and N,N-Dimethyacetamide (DMAC) under the trademark Surethane TM . The recommended coating technique is by application of a series of multiple thin coats and curing each coat prior to application of the next coat. Curing of each polyurethane coat is by placement of the coated unit for a selected time in a controlled temperature and moisture chamber and thereafter boiling, or soaking in room temperature water, known techniques which need no further description. The curing of the polyurethane coating 33 solidifies the liquid into a pliable and conforming surface. The soaking or boiling process also eliminates substances, such as the solvent (DMAC), that otherwise may be toxic to the patient. By altering polymer concentration, application thickness, and/or curing duration between coats, a customized coating or film thickness can be achieved.

The polyurethane coating thickness at 33 is preferably in the range of about 178 mm to 2 mm, for example about 1 mm.

The polyurethane coating material penetrates the front face 32 of the felted backing 30 to a sufficient extent as to satisfactually mechanically interlock therewith, but the major thickness of the backing 30 is not penetrated by the polyurethane coating. The polyurethane coating thus does not substantially stiffen the backing 30, which is left in a flexible and conformable condition in the finished repair piece 25.

Applicant has been informed by the supplier, that Surethane has been used on FDA approved permanent pacemaker lead systems and permanent neural stimulation electrodes, and a physical testing has shown a final tensile strength of over 5500 PSI with a 700% to 800% maximum strain and has shown a soft-segment elasticity of approximately 500%. The Surethane coating 33 thus provides the repair piece 25 with a tough and durable front face.

The felted Teflon TM backing layer 30 is of a smooth limp material which is readily conformable to flat or curved surfaces. Thus, the Teflon TM felted backing 30 can easily conform to the curved shape of the condyle 20 at the location of the removed articular cartilage portion 24. Further, the back face 31 of the Teflon TM felted backing 30 readily receives tissue ingrowth from the opposed face of the femur 11 so that, in time, the repair piece 25 can become fixedly interlocked to the femur 11 by tissue ingrowth to the backface 31 and into the felted Teflon TM backing 30.

The polyurethane coating 33 on the front face of the backing 30 is flexible and does not significantly reduce the conformability of the Teflon TM backing 30. The polyurethane coating 33 does, however, provide a smooth, slippery and very tough front surface on the front face of the rapair piece 25.

When lubricated by the lubricating liquid (synovial liquid) normally found within the joint, the front face 35 of the coating 33 provides a smooth and slippery sliding surface which simulates the front face of the natural undamaged articular cartilage 22 and is capable of sliding interaction with opposed tissue (for example, the lateral meniscus cartilage 16) and is readily slidable with respect thereto and rollable thereon without damaging such opposed tissue.

Ideally, the diameter (or width and length) of the repair piece 25 conforms closely to the opening 26 so that the repair piece 25 fits snugly in edge-to-edge relation with the surrounding articular cartilage layer 22. Also, the thickness of the repair piece 25 conforms generally to the depth of the defect. Thus, the repair piece 25 blends in as smoothly as possible with the surrounding cartilage 22 and will react with opposed tissue in the joint, as would have that portion 24 of the articular cartilage had it not been damaged and required replacement.

To hold the repair piece 25 in place at the repair site, until such time as it is anchored by normal tissue ingrowth from the underlying femur 11, several temporary fixation techniques have been developed.

Figure 5:
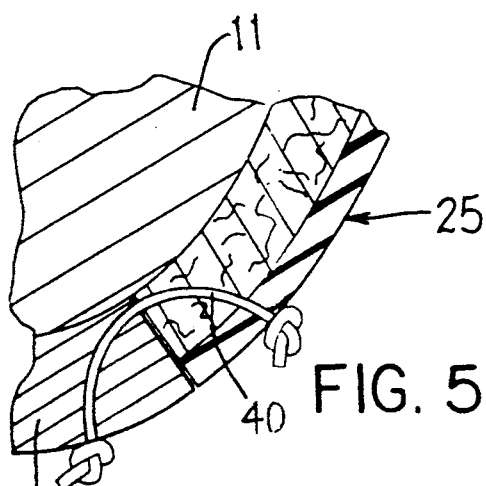
FIG. 5 is an enlarged fragment of FIG. 2 showing the repair implant initially affixed by suturing to adjacent articular cartilage.

One temporary fastening technique is shown in FIG. 5, in which sutures 40 are sewn through the edge portion of the repair piece 25 and the adjacent edge portion of the existing articular cartilage layer 22.

Figure 6:
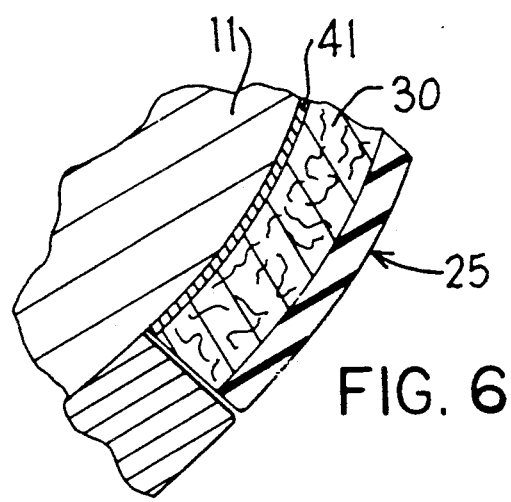
FIG. 6 is a fragment of FIG. 2 showing the repair implant initially affixed by adhesive bonding to the femur.

Alternately, as illustrated in FIG. 6, an adhesive layer 41 may be provided between the repair piece 25 and the opposed face of the tibia 11. The primary requirement is that the adhesive, while temporary, be effective for a sufficient time as to allow ingrowth of tissue from the tibia 11 into the fibrous backing 30 of the repair piece 25. In one instance, a two component (fibrinogen and thrombin) tissue sealant was used experimentally. The fibrinogen-thrombin sealant is a known biological substance that forms a clot and is sticky. This provides a kind of clotting-like bonding. The sealant is a two part bio-adhesive which can be applied using a dual syringe.

Figure 4:
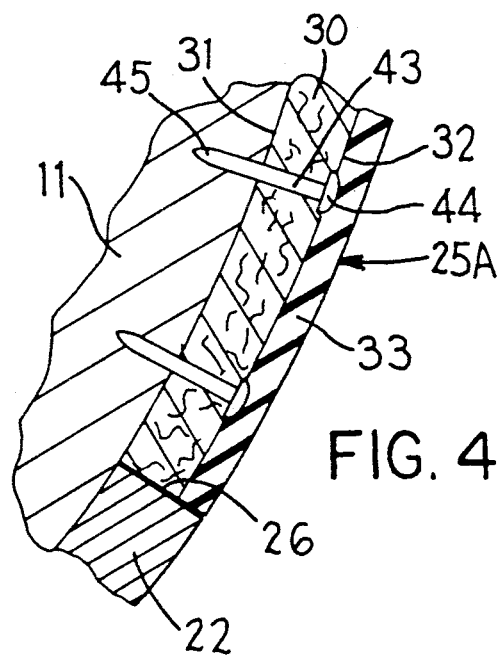
FIG. 4 is an enlarged fragment of FIG. 2 showing the repair implant initially affixed to the femur by elongated fasteners.

A further technique for temporarily fixing the repair piece 25 in place on the tibia 11, for a sufficient time to allow tissue ingrowth to permanently fix the repair piece 25, involves a modified repair piece 25A. In this instance, the repair piece 25A is modified during its construction as follows. Resorbable or non-resorbable pins 43 (FIG. 4) are pushed through the thickness of the felted backing 30 of the repair piece 25A from the front face 32 through the back face 31 so as to protrude beyond the latter. The polyurethane coating 33 is thereafter applied over the heads 44 of the resorbable pins 43 so as to anchor the pins in place in the repair piece 25A, and more particularly in the felted backing 30 thereof. To install the repair piece 25A in the opening 26 in the articular cartilage layer 22, the exposed inner ends 45 of the pins 43 are first applied against and pushed into the porous surface layer of the femur until the back face 31 of the backing 30 snugly contacts the opposed face of the femur 11 within the opening 26. The pins 43, if resorbable, stay in position long enough for tissue ingrowth from the femur 11 into the felted backing 30 to occur to a sufficient extent as to anchor the repair piece 25A in place. Resorbable suture material used to form the pins 43 may for example be polyglycolic acid or polylactic acid or a composite of both, both being conventional materials for making bioresorbable sutures. The pins in one example were about 1/32 inch diameter by ¼ inch long. The porous surface of the femur 11 under the articular cartilage 22 is soft enough to permit penetration by the exposed ends 45 of the pins.

While the pins 43 installed in this way are believed a particular suitable installation aid, it is also contemplated that other fasteners can be used, for example the pins 43 may be substituted by staples, nails, serrated pins, clamps, etc., of resorbable or suitable non-resorbable material. Such fasteners may have heads covered by the coating 33 as above described. Alternately, such fasteners may be simply driven through the entire thickness of the thickness of the pliable repair piece into the bone at the time of implant installation in the patient (with or without preformed holes in the repair piece for the fasteners) and the fasteners in this instance may also include screws since the screw heads would be accessible by a screw driver.

A further technique, for fixing the repair piece in place on the tibia 11, involves a further modified repair piece 25B. In this instance, after removal of the cartilage portion 24 including the damaged area, the opening 26 is continued down through the articular cartilage 22 and then extended at 51 into the underlying bone 11 by use of a suitable bone cutting tool of conventional type. The bottom portion of the recess 52 thus formed is undercut as indicated at 53 around its perimeter, leaving an overlying perimetral step 54 of bone. Such undercut recess 52 can readily be formed by a tool in the shape of a rotating milling cutter of radially extended character and of desired cross section, such as oval, trapezoidal, or, in the case of FIG. 7, rectangular cross section. Such tools are conventional and are capable of forming an undercut recess in more or less hard material in a well-known manner.

The repair piece 25B has a backing layer 30B which is sufficiently thick as to extend inward beyond the adjacent inner face of articular cartilage 22 and bone 11, and to the bottom of the recess 52. The backing layer 30B is thus expected to be thicker than the backing layer 30 above described in connection with FIGS. 4–6, for example.

Figure 7:
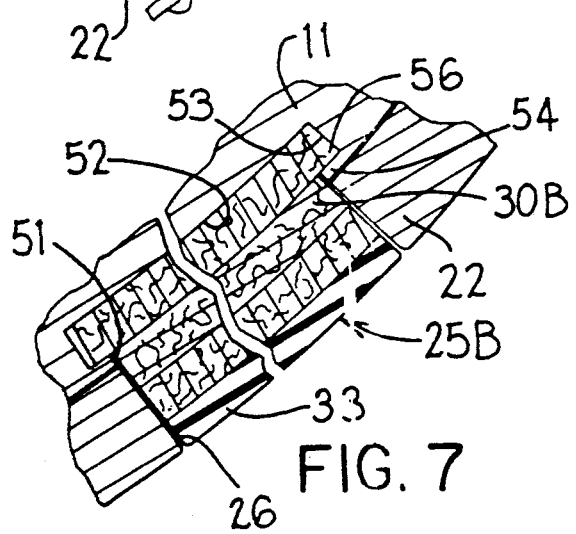
FIG. 7 is an enlarged fragment of FIG. 2 showing the repair implant initially affixed by mechanical interlocking in an undercut portion of the femur.

In addition, the backing layer 30B of FIG. 7 is of generally T-shaped cross section and is provided along its bottom (left end in FIG. 7) with diametrically extending flanges, or a radially extending circumferential flange, 56 for extending radially into the undercut 53 of the recess 52 in the bone 11. The thickened backing layer 30B is thus pushed into and snugly fills the undercut recess 52 in the bone 11 such that the flange 56 and step 54 mechanically interlock the repair piece 25B against accidental removal from the opening 26, prior to tissue ingrowth into the backing layer 30B providing a permanent interlock of the backing layer 30B to the articular cartilage 22 and/or bone 11. Indeed, the modified backing layer 30B, with its additional depth and flange 56, provides extra surface area for accepting tissue ingrowth.

The backing layer 30B can be formed by sculpting from an extra thick, single piece of backing layer material, if such is available. Alternatively, the thickened, flanged backing layer 30B can be built up from plural thinner lamina of backing material (conveniently, for example, corresponding to the thickness of the flange 56). Such backing layer lamina can be fixed together by any convenient means, such as by bonding (e.g. using material like the coating 33) or by sewing (the resulting stitches through the lamina of the backing layer 30B not being shown). In the latter variation, the backing layer 30B might have, for example, a bottom lamina of the thickness of the flange 56, an intermediate lamina approximately of the thickness of the step 54 and a top lamina which, with the coating 33, corresponds to the thickness of the surrounding articular cartilage 22. If stitching is used, it would be of non-resorbable material, such as non-resorbable suture material. Polyester thread would be a suitable choice.

It is contemplated that a combination of two or more of the above-discussed techniques of FIGS. 4–7 may be used for temporary fixation of a repair piece 25 or 25A or 25B to the femur 11 prior to permanent fixation by tissue ingrowth in the manner above described. For example, bone cement may be added between the repair piece and bone in FIGS. 4, 5 and 7 to further ensure fixed anchoring of the repair piece.

As a modification, it is contemplated that for some special instances it may suffice to provide an implant including a backing layer of the kind above discussed, but without the polyurethane coating 33 on the front face thereof. For example in an instance where it is contemplated that patient tissue may overgrow the front face of the implant, lack of the polyurethane coating 33 may allow the tissue overgrowth to interlock with the fibrous front face of the backing layer.

Although a particular preferred embodiment of the invention has been disclosed in detail for illustrative purposes, it will be recognized that variations or modifications of the disclosed apparatus, including the rearrangement of parts, lie within the scope of the present invention.

The embodiments of the invention in which an exclusive property or privilege is claimed are defined as follows:

1. An articular cartilage repair piece to be substituted for damaged articular cartilage on a bone in an articulated joint in a mammal, comprising:
a repair piece including a backing layer of nonwoven, felted fibrous material, the material being selected from the group consisting of PTFE and polyester, the backing layer being limp and readily conformable to flat and curved surfaces, the backing layer having a back face for application to the site of the damaged articular cartilage for eventual anchoring to the bone, the repair piece having a front face for opposing and coacting interface with adjacent material of the joint, said front face being defined by a coating of tough pliable material having a front surface which is smooth and is slippery in the presence of the natural synovial fluid in the joint, in which said coating is of polyurethane.

2. The apparatus of claim 1 in which the polyurethane coat is ½ to 2 mm thick.

3. The apparatus of claim 1 including means for temporarily fixing the repair piece in place of the removed piece of damaged articular cartilage.

4. The apparatus of claim 3 in which said temporary fixing means comprises sutures sewn through the edge portion of the repair piece and the adjacent edge portion of the existing natural articular cartilage layer left after removal of the cut-out piece.

5. The apparatus of claim 3 in which said temporary fixing means comprises an adhesive layer applied to said back face of said backing layer of said repair piece for application to and adhesion to bone exposed by removal of a piece of damaged articular cartilage.

6. The apparatus of claim 5 in which said adhesive layer is of a fibrinogen-thrombin adhesive.

7. The apparatus of claim 3 in which said temporary fixing means comprises resorbable fasteners extending at least through said backing layer, the fasteners extending through and beyond said back face of said backing layer so as to protrude beyond the latter and be insertable into the bone exposed by removal of the cut-out piece.

8. The apparatus of claim 3 in which said temporary fixing means comprises elongate discrete fasteners selected from the group consisting of pins, staples, nails, clamps and screws and extending at least out through the back of said backing layer to engage underlying bone.

9. The apparatus of claim 7 in which said fasteners consist of a material selected from the group consisting of polyglycolic acid or polylactic acid and a composite of polyglycolic and polylactic acids, the pins being approximately 1/32 of an inch in diameter and ¼ inch long.

10. The apparatus of claim 3 in which said temporary fixing means comprises flange means extending radially beyond a rear most portion of said backing layer and adapted to mechanically lock in an undercut opening in bone beneath the damaged articular cartilage to be replaced by said repair piece.

11. An articular cartilage repair piece to be substituted for a piece of damaged articular cartilage on a bone in an articulated joint in a mammal, comprising:
a repair piece including a backing layer of nonwoven, felted fibrous material, the backing layer being limp and readily conformable to flat and curved surfaces, the backing layer having a back face for application to the face of the bone exposed by removal of a portion of the articular cartilage containing the damaged area and for eventual anchoring to the bone by tissue ingrowth from the bone, the repair piece having a front face for slidably opposing and coacting with adjacent material of the joint generally in the manner of the front face of the natural articular cartilage, the backing layer being of PTFE and about 1.2 mm thick, the front face being defined by a coating of tough rubbery material having a front surface which is smooth and is slippery in the presence of the natural synovial fluid in the joint, the coating being of polyurethane and being about ½ to 2 mm thick, and including means for temporarily fixing the repair piece in place of the piece of damaged articular cartilage.

12. In a repair for a damaged portion in an articular cartilage layer fixed to and protectively coating a bone surface in an articulated joint of a mammal, wherein the damaged portion of the articular cartilage layer has been cut away to leave a hole of desired shape and area through the articular cartilage layer, at the bottom of which hole a corresponding area of underlying bone is exposed, the surfaces bounding the hole thus being defined by the surrounding articular cartilage layer and the exposed underlying bone, and wherein the articular cartilage layer has (1) a back side continuously fixed to a substantial surface area of the bone in such articulated joint and has (2) a front face facing another component of the joint in mutually slidable relation therewith, which front face has a smooth surface which is slippery in the presence of the usual synovial fluid present in the articulated joint, such repair comprising:
a plug of thickness corresponding to the thickness of the articular cartilage surrounding the hole and of shape and area corresponding to the shape and area of the hole, said plug being a laminate including:
(A) a backing layer having means for facing and engaging the bone exposed at the bottom of the hole and receiving tissue ingrowth from said bone exposed at the bottom of the hole, the last-mentioned means defining the back face of said backing layer and comprising exposed fibers of felted material, said backing layer further having means for facing and engaging the articular cartilage forming the periphery of the hole and for receiving tissue ingrowth therefrom, the last-mentioned means defining the peripheral face of said backing layer of said plug and comprising exposed fibers of felted material, said backing layer being formed by a layer of said felted material, said material being a non-woven, non-mesh fibrous material, the backing layer being limp and readily conformable to flat and curved surfaces;
(B) means for simulating the front face of the articular cartilage and comprising a synthetic coating of tough rubbery material which is smooth, said coating being slippery in the presence of the natural synovial fluid of the joint, said coating having means for flushly and smoothly continuing the front face of the articular cartilage layer across the hole in such articular cartilage layer; and (C) means for engaging surfaces bounding the hole in the articular cartilage layer and temporarily fixing the plug in the hole while awaiting tissue ingrowth to permanently fix said plug in said hole.

13. The apparatus of claim 12 in which the material of said backing layer is selected from the group consisting of PTFE and polyester.

14. The apparatus of claim 12 in which said means for simulating the front face of the articular cartilage and defining said coating is of polyurethane.

15. The apparatus of claim 12 in which the means for temporarily fixing the plug in the hole is an adhesive means interpositioned between the opposed surface of the plug and the tissue bounding the hole.

16. The apparatus of claim 15 in which said adhesive layer is of fibrinogen-thrombin glue.

17. The apparatus of claim 12 in which said means for temporarily fixing the plug in the hole comprises means for insertion at least through said backing layer and into the bone at the bottom of the hole, such means for insertion comprising pins of bioabsorbable material.

18. The apparatus of claim 17 in which said means temporarily fixing the plug in the hole further includes a fibrinogen-thrombin glue located on said plug for engagement with tissue defining the hole.

* * * * *

UNITED STATES PATENT AND TRADEMARK OFFICE
CERTIFICATE OF CORRECTION

PATENT NO. : 5 067 964
DATED : November 26, 1991
INVENTOR(S) : James W. RICHMOND et al It is certified that error appears in the above-identified patent and that said Letters Patent is hereby corrected as shown below:

Column 4, line 9; change "178" to ---1/2---.

Column 4, line 44; change "rapair" to ---repair---.

Signed and Sealed this

First Day of June, 1993

Attest:

MICHAEL K. KIRK

Attesting Officer

Acting Commissioner of Patents and Trademarks